United States Patent [19]

Castberg et al.

[11] Patent Number: 5,213,759

[45] Date of Patent: May 25, 1993

[54] STERILIZATION

[75] Inventors: Helge B. Castberg, Kolbotn, Norway; Nigel A. Chant, Stotfold, United Kingdom

[73] Assignee: Elopak Systems A.G., Glattbrugg, Switzerland

[21] Appl. No.: 644,116

[22] Filed: Jan. 18, 1991

Related U.S. Application Data

[63] Continuation of Ser. No. 347,739, May 5, 1989, abandoned.

[30] Foreign Application Priority Data

May 5, 1988 [GB] United Kingdom ................. 8810603

[51] Int. Cl.$^5$ .......................... A61L 2/10; A61L 2/20
[52] U.S. Cl. ........................................ 422/24; 422/27; 422/28; 422/29; 250/455.11
[58] Field of Search ....................... 422/23, 24, 27, 28, 422/29; 250/455.1, 455.11

[56] References Cited

U.S. PATENT DOCUMENTS

| | | | |
|---|---|---|---|
| 3,117,832 | 1/1964 | Thomas | 422/24 X |
| 4,169,123 | 9/1979 | Moore et al. | 422/28 X |
| 4,175,140 | 11/1979 | Bachmann et al. | 422/24 X |
| 4,289,728 | 9/1981 | Peel et al. | 422/24 X |
| 4,609,471 | 9/1986 | Beemster et al. | 422/24 X |
| 5,011,664 | 4/1991 | Olanders | 422/292 |
| 5,114,670 | 5/1992 | Duffey | 422/24 |

Primary Examiner—Jill A. Johnston
Attorney, Agent, or Firm—Reising, Ethington, Barnard, Perry & Milton

[57] ABSTRACT

In a method of sterilizing micro-organisms, the micro-organisms are subjected to UV radiation, in a wavelength band which kills micro-organisms, while in an atmosphere of inert gas or of ozone.

17 Claims, No Drawings

STERILIZATION

This is a continuation of application Ser. No. 347,739, filed on May 5, 1989 and now abandoned.

BACKGROUND OF THE INVENTION

1. Field of the Invention

This invention relates to a method of sterilization and to a substance sterilized by the method. It has general application, but particular application to packaging.

2. Description of the Prior Art

U.S. Pat. No. 4,122,134 discloses a method of and system for packaging commercially sterile foods by placing the sterile food in a plastics container tending towards opacity to visible light radiation and tending towards transparency to ultraviolet radiation. The container is open and the food product is cooled to a temperature slightly above the freezing point of water preparatory to and while in a chamber having an atmosphere of cooled, dry inert, sterile gas, preferably nitrogen, carbon dioxide, or a mixture thereof. In the chamber, the inert gas and food product are irradiated by ultraviolet energy that propagates through the container. The container is sealed in the chamber, whereby the inert atmosphere is maintained on the surface of the food product while stored in the container, at temperatures slightly above the freezing point of water for prolonged time periods.

The purpose of the introduction of the nitrogen and/or carbon dioxide is to remove air and thus oxygen from around the container and from around the food product within the container and also to remove water vapour from around the container and from around the food product, thereby to avoid condensation thereon.

U.S. Pat. No. 3,769,517 discloses apparatus which permits treatment of products with ultraviolet light in a controlled atmosphere and which comprises a chamber having inlet and outlet openings for the passage of a product to be treated, one or more ultra-violet lamps, and at least one gas reservoir within the chamber separated by a foraminous panel. Gas, for example nitrogen, or a nitrogen/oxygen mixture, is introduced into the reservoir, passes through the foraminous panel and over and around the path of travel of a workpiece to be treated.

The nitrogen atmosphere, when employed alone, is again used to remove air and thus oxygen from around the workpiece. The nitrogen also reduces hazards such as the possibility of fire or explosion and the production of ozone during the treatment process.

DE222006A discloses the use of high-energy ionizing radiation for the sterilization of nutrient media for the purpose of assisting the growth of multicellular animal cells and in particular of mammalian cells in vitro.

The use of such ionizing radiation is much more cumbersome than the use of UV radiation, because ionizing radiation requires far greater shielding of the operators from the source of the radiation. An inert gas, such as nitrogen or helium, is used to remove air and thus oxygen from the atmosphere surrounding the nutrient medium in order to avoid degradation of the nutrients in the medium owing to the presence of oxygen. The inert gas also assists in keeping moisture away from the nutrient medium to maintain the nutrient medium completely dry during irradiation.

The patent discloses that a synergistic result is produced by the combination of the steps of irradiating a food product with UV energy for sterilisation and packaging in an inert atmosphere and that certain deleterious colonies of bacteria and possibly other colonies actually decrease in number at the same time that their further growth is inhibited by the combination of the UV radiation and encapsulation or packaging with the inert gas.

Derwent File Supplier No. AN 85-234441(JP60153982) appears to disclose the removal of contamination compounds from the surface of articles by flowing water containing dissolved ozone over the surfaces under the irradiation of UV. The water can contain dissolved ozone or bubbles of ozonized gas.

Where the contamination compounds are organic compounds, they are partially oxidized by the treatment, aldehydes, ketones and carboxylic acids being forces, and removed by the water. Where the contamination compounds are inorganic compounds, they dissolve or disperse in the water and are thus removed.

Ozone is decomposed under the irradiation of UV to form an oxygen radical, an hydroxyl radical and a hydrogen peroxide radical. As such radicals have high activity but short life-time, the treatment generates the radicals on the surfaces themselves and so makes them most effective. The washing effect is further promoted because the reactivity of the contamination compounds can be enhanced by the UV irradiation, thus breaking down the compounds into smaller particles and into more hydrophilic compositions. The washing effect was enhanced with increasing washing time and with increasing ozone dissolved concentration. Use of oxygen gas in ozone generation increased the ozone concentration and enhanced the washing effect.

Such treatment is concerned with removing contamination from the surface of articles and is not concerned with sterilization in which micro-organisms are rendered not-viable.

U.S. Pat. No. 4,309,388 discloses sterilizing apparatus which comprises an enclosure surrounding the top, bottom and sides of a central sterilizing enclosure space and adjacent inlet and outlet enclosure spaces opening horizontally to the exterior of the enclosure at the opposite ends thereof. A continuously moving conveyor carries open-topped glass bottles to be sterilized horizontally through the inlet, sterilizing and outlet enclosure spaces of the enclosure. The sterilizing enclosure space is divided by partition walls into an upper compartment which opens at the bottom thereof into a lower compartment immediately above the path of travel of the open tops of the bottles passing through the lower compartment of the sterilizing enclosure space. Ozone-generating ultraviolet lamps are mounted in the upper compartment and a blower circulates air between the lower and upper compartments and through the opening of the upper compartment into the lower compartment so that ozone generated in the upper compartment is directed into the openings at the tops of the bottles moving in the lower compartment. Ozone decomposition accelerating ultra-violet lamps are positioned in the inlet and outlet enclosure spaces to accelerate decomposition of the ozone in the air escaping to the surrounding atmosphere through the inlet and outlet enclosure spaces.

The UV employed for the purpose of indirectly sterilizing the bottles has a radiation wavelength which is predominantly that in the wavelength band which generates ozone and not in the wavelength band which kills micro-organisms. Although UV radiation predominantly in the wavelength band which kills micro-organisms is employed, it is not employed for the purpose of rendering the micro-organisms non-viable but simply in order to degrade the ozone after its production.

CH387881 discloses a sterilization system in which the objects to be sterilized are subjected in an enclosure to the simultaneous actions of (1) vapors of a bactericidal substance, for example Methanogene, Trioxymethylene and Aldylene, (2) ozone generated in the enclosure by a lamp radiating at a wavelength of 185 nm. and (3) UV radiation of a wavelength of 253.7 nm.

In CH387881, the primary action of the ozone is particularly for the benefit of the operator of the system, in that it deodorizes the vapours from the bactericidal substance and removes their causticity from them, without however modifying their toxicity. This primary action is accomplished by a secondary action in which the effect of the ultraviolet radiation is to produce an activation of the bactericidal action, not only of the ozone but also of the bactericidal vapours.

Patent Abstracts of Japan, Vol.12, No.22 (C-470) (2869) (JP 62-176595A) discloses a method of decomposing a low molecular organic substance by adding ozonated water to a mixture of hydrogen peroxide, and waste water containing the organic substance, while the whole is irradiated with UV. It is not directed to the sterilization of micro-organisms.

In U.S. Pat. No. 4,336,125, a long sheet material to be sterilized is passed through an atmosphere of $H_2O_2$ mist of low concentration and of droplet particle size of approximately 10 microns at room temperature for approximately one second and is then irradiated for approximately one second with UV lamps positioned to irradiate opposite surfaces of the sheet material, whereby the material is sterilized as a result of the synergistic effect produced by the combination of these two sterilization steps.

SUMMARY OF THE INVENTION

According to one aspect of the present invention, there is provided a method of sterilization which comprises subjecting micro-organisms to UV radiation through an atmosphere comprised substantially wholly of inert gas, so as to obtain a synergistic effect between the UV radiation and said atmosphere and to render the micro-organisms non-viable.

According to a second aspect of the present invention, there is provided a substance which has been sterilized by a method comprised of subjecting a micro-organisms present at said substance to UV radiation through an atmosphere comprised substantially wholly of inert gas, with a synergistic effect having been obtained between said UV radiation and said atmosphere.

We have discovered such synergistic effect, which we believe to be hitherto unsuspected, in experiments which we carried out with a view to ascertaining whether such synergistic effect might be obtained. We found that it consists in that the effect of the use of UV radiation through such inert gas atmosphere under a predetermined set of conditions, insofar as its rendering of micro-organisms non-viable is concerned, is greater than the sum of the effects of subjecting micro-organisms to an identical atmosphere under that same set of conditions and of subjecting micro-organisms to identical UV radiation through an atmosphere of air under that same set of conditions.

We believe that the use of inert gas instead of air improves the killing efficiency of the UV radiation at the micro-organisms.

According to a third aspect of the present invention, there is provided a method of sterilization which comprises subjecting micro-organisms to UV radiation in the presence of ozone so as to render the micro-organisms non-viable, the UV radiation being predominantly in the wavelength band which kills micro-organisms.

According to a fourth aspect of the present invention, there is provided a substance which has been sterilized by a method comprised of subjecting micro-organisms present at said substance to UV radiation in the presence of ozone, the UV radiation having been predominantly in the wavelength band which kills micro-organisms.

We have found that the use of UV in an ozone atmosphere instead of in air gives an improved killing efficiency of micro-organisms. Moreover, we have not needed to employ a bactericidal substance in addition to the ozone.

According to a fifth aspect of the present invention, there is provided a method of sterilization which comprises subjecting micro-organisms to UV radiation through an atmosphere comprised of substantially other than air, so as to obtain a synergistic effect between the UV radiation and said atmosphere and to render the micro-organisms non-viable.

In the present invention, "inert gas" means a gas or a mixture of gases which is not substantially degraded by exposure to UV radiation of bactericidal intensity.

The inert gas can be chosen from the group consisting of nitrogen, argon, helium, neon, crypton and xenon. Nitrogen is preferred because of its relative cheapness.

In the present specification, "ozone" means a gas comprised of significant amounts of $O_3$ radicals and hydroxyl radicals.

The ozone employed is preferably produced by subjecting air to a photoflux in the vacuum ultraviolet range, which photons have between 8–10 ev and ionize only the oxygen content, forming various activated oxygen compounds in the gas phase. Such activated oxygen is advantageously PHOTOZONE (Registered Trade Mark) gas which is produced by the PHOTOZONE (Registered Trade Mark) lamp obtainable from Water Management A/S of Oslo, Norway.

Such activated oxygen has a relatively greater oxidation potential than ozone produced by the classical method of employing a high voltage of between 8,000 and 10,000 volts across electrodes, and thus a greater killing power of micro-organisms, owing to its higher proportion of hydroxyl radicals.

The present invention is particularly useful for the sterilization of food contact surfaces. Such surfaces can be the inside surfaces of walls, sheets, films, cups and cartons. Where they are the inside surfaces of cartons ready to be filled, they may be for example liquid contact surfaces of cartons formed from paperboard (or from paperboard and aluminium foil, or from paperboard and polymer) with internal and external plastics coatings. Such liquid can be long-life milk or orange juice, for example.

Tests in which the food contact surfaces of cartons were subjected to UV-C and were contained in either an inert gas atmosphere or an ozone atmosphere appear to show a synergistic effect between the UV-C and the inert gas, or between the UV-C and the ozone.

An important commercial advantage of the invention is that the required kill rates of exposed micro-organisms are achieved by treatment times significantly less than with known sterilization methods.

treatments in each Example being given in their actual sequence.

TABLE I

| EXAMPLE NO. | TREATMENT | INOCULUM | DECIMAL REDUCTION |
|---|---|---|---|
| 1A | Air + UV-C 254 nm (6s) | $5.9 \times 10^5$ | 4.0 |
| 2A | Air + $N_2$ (3l) | $5.9 \times 10^5$ | ≃0 |
| 3A | Air + $N_2$ (3l) + UV-C 254 nm (6s) | $5.9 \times 10^5$ | 4.5 |
| 1B | Air + UV-C 254 nm (6s) | $6.3 \times 10^4$ | 3.4 |
| 2B | Air + $N_2$ (3l) | $6.3 \times 10^4$ | ≃0 |
| 3B | Air + $N_2$ (3l) + UV-C 254 nm (6s) | $6.3 \times 10^4$ | 4.0 |
| 4A | Air + 2% $H_2O_2$ (150 mg) + UV-C 254 nm (12s) | $3.9 \times 10^6$ | <3.0 |
| 4B | Air + 2% $H_2O_2$ (150 mg) + $N_2$ (3l) + UV-C 254 nm (3s) | $3.9 \times 10^6$ | 4.0 |
| 5A | Air + 2% $H_2O_2$ (150 mg) + UV-C 254 nm (3s) + heat 150° C. (2.6 s) | $2.7 \times 10^6$ | 5.3 |
| 5B | Air + 2% $H_2O_2$ (150 mg) + $N_2$ (3l) + UV-C 254 nm (3s) + heat 150° C. (2.6s) | $2.7 \times 10^6$ | 5.8 |
| 6A | Air + 2% $H_2O_2$ (150 mg) + UV-C 254 nm (3s) + Steam (3s) | $3.0 \times 10^6$ | 5.2 |
| 6B | Air + 2% $H_2O_2$ (150 mg) + $N_2$ (3l) + UV-C 254 nm (3s) + Steam (3s) | $3.0 \times 10^6$ | 5.7 |
| 6C | Air + 2% $H_2O_2$ (150 mg) + $N_2$ (3l) + UV-C 254 nm (3s) + heat 150° C. (2.6s) + Steam (3s) | $3.0 \times 10^6$ | 6.4 |
| 7A | Air + Ozone (3l) | $6.2 \times 10^6$ | <1.0 |
| 7B | Air + $H_2O$ (150 mg) + Ozone (3l) | $6.2 \times 10^6$ | <1.0 |
| 7C | Air + $H_2O$ (150 mg) + Ozone (3l) + UV-C 254 nm (9s) | $6.2 \times 10^6$ | 4.4 |
| 7D | Air + 2% $H_2O_2$ (150 mg) + Ozone (3l) + UV-C 254 nm (9s) | $6.2 \times 10^6$ | 5.6 |
| 8A | Air + Ozone (3l) + UV-C 254 nm (3s) + heat 150° C. (2.6s) | $2.7 \times 10^6$ | 3.8 |
| 8B | Air + 2% $H_2O_2$ (150 mg) + Ozone (3l) + UV-C 254 nm (3s) + heat 150° C. (2.6s) | $2.7 \times 10^6$ | 5.3 |

Tests in which the food contact surfaces of cartons were subjected not only to UV-C in an inert gas or ozone atmosphere but also to a pre-spray of $H_2O_2$ appear to show additional synergism with consequential further improvement in treatment times.

The wavelength band of the UV radiation is advantageously substantially greater than 200 nanometers, preferably between 220 and 330 nanometers.

DESCRIPTION OF THE PREFERRED EMBODIMENTS

In order that the invention may be clearly understood and readily carried into effect, examples of known sterilization treatments and of sterilization treatments according to the invention will now be described.

EXAMPLES 1-8

These Examples set forth in Table I are a selection of various comparable tests and illustrate the killing efficiency of exposure of *B. subtilis var. globigii* (B-17) to UV-C (254 nm), 2% $H_2O_2$, and/or heat, under various atmospheres. Air is mentioned at the commencement of all Examples because it was the initial atmosphere and remained so unless and until purged by the introduction of stream, $N_2$, or ozone, which latter remain the atmosphere unless and until purged by steam.

The tests were performed in gable-top, aluminium-foil-lined cartons, not top-sealed. The distance from the UV-C light source and the $H_2O_2$ spray nozzle tip to the base of the cartons was a maximum of 28 cm.

Cartons were prior to the test inoculated with the spore suspension to a level of approximately $10^6$ spores per carton. Rinsing with plating was used to determine the spore load of the carton.

After exposure to the various combination of treatment, cartons were treated with catalase to remove residual $H_2O_2$. Cartons were then covered with nutrient agar on the inside and incubated for counting survivors.

The conditions and exposure times for the tests are given in Table 1 together with the results, the various in each appropriate Example, the carton was flushed with $N_2$, supplied at 2.4 l/s, for 1.6 s, or with Photozone, supplied at 0.8 l/s, for 5.0 s.

Examples 1A to 3A show the synergistic effect of passing UV-C through an $N_2$ atmosphere, as do Examples 1B to 3B. Examples 4A and 4B illustrate the synergistic effect of passing UV-C through an $N_2$ atmosphere introduced immediately after the introduction of an $H_2O_2$ mist. Examples 5A and 5B illustrate that the latter synergistic effect is maintained with the final application of heat. Examples 6A to 6C show that the synergistic effect is maintained with the final application of steam, or of heat and then steam.

Examples 7A to 7D illustrate the very great improvement obtained by the passage of UV-C through a moist ozone atmosphere and the further improvement obtained by the employment of an $H_2O_2$ spray instead of a water spray. Examples 8A and 8B illustrate the great improvement obtained by prior addition of $H_2O_2$ compared with passing UV-C through a dry ozone atmosphere.

Examples 1A, 1B, 4A, 5A and 6A are illustrative of known treatments. Examples 3A, 3B, 4B, 5B, 6B, 6C, 7C, 7D, 8A and 8B are illustrative of the present invention. The time periods given in each Example are sequential rather than concurrent.

Testing was also carried out on the spores *Aspergillus niger* as these are known to be highly resistant to ultraviolet radiation. These tests were carried out in the form of a control to help justify previous results.

EXAMPLES 9 AND 10

These examples illustrate the killing efficiency of a preferred treatment, namely UV-C (254 nm), 2% $H_2O_2$, heat and nitrogen atmosphere on surfaces covered with a spore suspension of *Aspergillus niger*.

The actual test procedure was similar to that described in relation to Examples 1-8. Spore suspension of *Aspergillus niger* was swabbed onto the inner surface of the carton. The conditions and spore kill rate are given in Table 2.

TABLE 2

| EXAMPLE | TREATMENT | INOCULUM | DECIMAL REDUCTION |
|---|---|---|---|
| 9. | Air + 2% $H_2O_2$ (150 mg) + $N_2$ (6s) + UV-C 254 nm (3s) + heat 150° C.(2.5s) | $7 \times 10^5$ | 3.7 |
| 10. | Air + 2% $H_2O_2$ (150 mg) + $N_2$ (6s) + UV-C 254 nm (3s) + heat 150° C.(2.5s) | $8 \times 10^4$ | 3.3 |

Spore Preparation

*Aspergillus niger* spores were inoculated on Malt extract agar and incubated at 25° C. for one week.

Spores were harvested using a sterile loop and suspended in ¼ strength Ringer's solution with Tween 80 to achieve a concentration of approximately $10^5$–$10^6$ spores/ml. Spores were applied to the surfaces by means of a cotton wool swab. Carton surfaces were dried overnight followed by exposure to the sterilizing test conditions.

*Bacillus subtilis var. globigii* B17 spores were grown and isolated.

UV-C—Sources

The UV-C source was IWASAKI irradiation equipment (254 nm—UV-C) consisting of a high intensity sterilizer GHS 490145, nine lamp sets GHL 400-2 and three irradiator sets GE 4301.

Ozone was produced by a Photozone lamp (185 nm—UV-C) from Water Management A/S.

Methods of Inoculation and Organisms

*B.subtilis var. globigii* (B17) arc known to be highly resistant to hydrogen peroxide and ultra-violet radiation.

The method of producing a carbon loading of $10^6$ was as follows. A stock suspension of approximately $10^9$/ml dilution was sprayed into the carton in 0.5 ml doses, where the residual in the carton is approximately $10^6$. The cartons were then dried overnight, and the verification of actual bacteriological loading was carried out on ¾ cartons. 9 ml of 0.25 strength "Ringers" solution was poured into the carton, the latter closed and shaken vigorously and approximately 20 seconds was allowed for the solution to collect into the base of the carton 1 ml. was removed by pipette and further dilutions were carried out.

Spray System

It was detected to use a device already to use, which proved to give excellent coverage on a 1 liter "Pure-Pak" carton. This device is commercially available from Metal Box plc of Reading, Berkshire, United Kingdom.

Spray Parameters

Inlet air pressure = 90 psi. (6.4 kg/sq cm.)
Atomising Air = 80 psi. (5.6 kg/sq cm.)
Pulse air pressure = 60 psi. (4.2 kg/sq cm.)
Tank pressure = 20 psi. (1.5 kg/sq cm.)
Discharge air pressure = 10 psi. (1.05 kg/sq cm.)
Nozzle tip to carton base = 270–280 nm.

This setting remained standard throughout all of the testing where spraying of $H_2O_2$ was required. The only change was to the duration of the spraying time, which was varied to give differing levels of $H_2O_2$ within the carton.

We claim:

1. A method of sterilisation which comprises subjecting micro-organisms at a surface of packaging material, which surface will be brought into contact with product to be packaged, to UV radiation through an atmosphere in contact with said micro-organisms and comprised substantially wholly of inert gas, which inert gas is a gas or a mixture of gasses which is not substantially degraded by exposure to UV radiation of bactericidal intensity, so as to obtain a synergistic effect between the UV radiation and said atmosphere and to render the micro-organisms non-viable, said micro-organisms being subjected to said radiation before said surface of said packaging material is brought into contact with said product.

2. A method according to claim 1, and further comprising subjecting said micro-organisms to UV radiation additionally in the presence of hydrogen peroxide.

3. A method according to claim 1, and further comprising subjecting said micro-organisms to UV radiation additionally in the presence of a low concentration of hydrogen peroxide so as to obtain a synergistic effect between the UV radiation and the hydrogen peroxide in rendering the micro-organisms non-viable.

4. A method according to claim 1, and further comprising subjecting said micro-organisms to heat.

5. A method of sterilization which comprises operating an UV radiation producing device to produce UV radiation, operating an ozone producing device to produce an ozone-comprising gas which is comprised of significant amounts of $O_3$ radicals and hydroxyl radicals and subjecting micro-organisms to said UV radiation in the presence of said ozone so as to render the micro-organisms non-viable and so as to obtain a synergistic effect between the UV radiation and the ozone insofar as the rendering of the micro-organisms non-viable is concerned, the UV radiation being predominantly in the wavelength band which kills microorganisms.

6. A method according to claim 5, in which said wavelength band is substantially greater than 200 nanometers.

7. A method according to claim 6, in which said wavelength band is between 220 and 330 nanometers.

8. A method according to claim 5, wherein the micro-organisms are subjected to UV radiation additionally in the presence also of moisture.

9. A method according to claim 8, wherein said moisture is provided by a spray of water.

10. A method according to claim 8, wherein said moisture is provided by steam.

11. A method according to claim 5, wherein said micro-organisms are subjected to UV radiation while at a surface of a packaging material.

12. A method according to claim 5, and further comprising subjecting said micro-organisms to UV radiation additionally in the presence also of hydrogen peroxide.

13. A method according to claim 5, and further comprising subjecting said micro-organisms to UV radiation additionally in the presence of a low concentration of hydrogen peroxide so as to obtain a synergistic effect between the UV radiation and the hydrogen peroxide in rendering the micro-organisms non-viable.

14. A method according to claim 5, and further comprising subjecting said micro-organisms to heat.

15. A method of sterilization which comprises subjecting micro-organisms to UV radiation in the presence of hydrogen peroxide and through an atmosphere comprised substantially wholly of inert gas, which inert gas is a gas or a mixture of gases which is not substantially degraded by exposure to UV radiation of bactericidal intensity, so as to obtain a synergistic effect between the UV radiation and said atmosphere and to render the micro-organisms non-viable.

16. A method according to claim 15, wherein a synergistic effect is obtained between the UV radiation and the hydrogen peroxide in rendering the micro-organisms non-viable.

17. A method according to claim 15, and further comprising subjecting said micro-organisms to heat.

* * * * *